(12) United States Patent
Hay

(10) Patent No.: US 8,857,749 B2
(45) Date of Patent: Oct. 14, 2014

(54) DUAL-CUTTING BONE MILL

(75) Inventor: James Scott Hay, Parkland, FL (US)

(73) Assignee: Bruxx Bone Mills Corporation, Delray Beach, FL (US)

( * ) Notice: Subject to any disclaimer, the term of this patent is extended or adjusted under 35 U.S.C. 154(b) by 1002 days.

(21) Appl. No.: 12/915,934

(22) Filed: Oct. 29, 2010

(65) Prior Publication Data

US 2011/0106090 A1 May 5, 2011

Related U.S. Application Data

(60) Provisional application No. 61/256,055, filed on Oct. 29, 2009.

(51) Int. Cl.
*B02C 19/22* (2006.01)
*A61F 2/46* (2006.01)

(52) U.S. Cl.
CPC ....... *A61F 2/4644* (2013.01); *A61F 2002/4645* (2013.01)
USPC ........................................ 241/260.1; 241/100

(58) Field of Classification Search
USPC ............................ 241/2, 260.1, 261, 100, 236
See application file for complete search history.

(56) References Cited

U.S. PATENT DOCUMENTS

| | | | |
|---|---|---|---|
| 1,535,772 A | 4/1925 | Haufler | |
| 2,001,075 A | 5/1935 | Sundstrand | |
| 2,048,509 A | 7/1936 | Melcher et al. | |
| 4,231,527 A | 11/1980 | Bounds | |
| 4,307,846 A | 12/1981 | Spelsberg | |
| 4,715,545 A | 12/1987 | Hanifl et al. | |
| 4,878,626 A * | 11/1989 | Leuthold et al. | 241/57 |
| 4,925,117 A * | 5/1990 | Ramos | 241/236 |
| 4,951,887 A * | 8/1990 | Gutnecht | 241/260.1 |
| 5,188,301 A * | 2/1993 | Hasegawa | 241/33 |
| 5,381,730 A * | 1/1995 | Kim | 99/510 |
| 5,396,836 A * | 3/1995 | Kim | 99/510 |
| 5,452,650 A * | 9/1995 | Lee | 99/510 |
| 5,533,683 A | 7/1996 | Fay et al. | |
| 5,607,269 A | 3/1997 | Dowd et al. | |
| 5,622,323 A * | 4/1997 | Krueger et al. | 241/101.76 |
| 5,769,853 A * | 6/1998 | Quetin | 606/85 |
| 5,791,572 A | 8/1998 | Fernlund | |
| 5,918,821 A * | 7/1999 | Grooms et al. | 241/27 |
| 6,287,312 B1 | 9/2001 | Clokie et al. | |
| 6,357,682 B1 * | 3/2002 | Hext | 241/161 |
| 6,390,399 B1 | 5/2002 | Mankiewicz | |
| 6,402,070 B1 | 6/2002 | Ishida et al. | |
| 6,464,156 B1 | 10/2002 | Wexell | |
| 6,484,954 B2 | 11/2002 | Lenox | |
| 6,755,365 B1 | 6/2004 | Meredith | |
| 7,028,933 B2 * | 4/2006 | Maiz | 241/101.8 |
| 7,156,329 B2 | 1/2007 | Hay et al. | |
| 2002/0014547 A1 * | 2/2002 | Schwelling | 241/30 |

* cited by examiner

*Primary Examiner* — Faye Francis
(74) *Attorney, Agent, or Firm* — Laurence A. Greenberg; Werner H. Stemer; Ralph E. Locher

(57) ABSTRACT

A tissue processing device, including a housing defining a first passage through at least a portion thereof, the first passage defining a longitudinal axis; a first processing member rotatably coupled to the housing and extending across at least a portion of the first passage; and a second processing member rotatably coupled to the housing and extending across at least a portion of the first passage, the second processing member being substantially parallel to the first processing member, the second member being offset from the first processing member in a first direction substantially parallel to the longitudinal axis and in a second direction substantially transverse to the longitudinal axis.

13 Claims, 5 Drawing Sheets

US 8,857,749 B2

DUAL-CUTTING BONE MILL

CROSS-REFERENCE TO RELATED APPLICATION

This application is related to and claims priority to U.S. Provisional Patent Application Ser. No. 61/256,055, filed on Oct. 29, 2009, entitled "Dual Cutting Bone Mill," the entirety of which is incorporated herein by reference.

STATEMENT REGARDING FEDERALLY SPONSORED RESEARCH OR DEVELOPMENT n/a

FIELD OF THE INVENTION

The present invention relates to a tissue processing device and methods of use thereof, and in particular, to a method and device for cutting or processing bone material for use during an orthopedic procedure.

BACKGROUND OF THE INVENTION

Numerous medical procedures involve the use of processed tissue samples as grafts to fill in or otherwise promote growth and healing at a surgical site. For example, orthopedic surgery often employ the infusion of a mixture crushed or milled bone with blood or other biological and/or pharmaceutical components into a surgical site to promote healing and recovery after an injury and the procedure itself. The crushed or milled bone is typically obtained from a larger bone specimen of the patient and then processed using a bone grinder or cutter that reduces the larger specimen into crushed bone particles more suitable for use in the surgical procedure. Processing and incorporating a patient's own tissue alleviates the possibility of rejection or infection at the surgical site. The surgeon can thus utilize the processed bone particles and/or combinations thereof with other growth-promoting agents to repair bone defects or injuries.

Existing bone mills are typically large, expensive devices that are cumbersome to use and clean and often require re-sterilization at the end of each use. The need to re-sterilize can require expensive and time consuming gas sterilization or autoclave sterilization procedures, which can limit the overall availability of the mill for multiple procedures in any given time period. The unavailability of such devices increases the time which necessarily passes between procedures, thereby decreasing operating room and surgical efficiency. Further, the porous nature of blades commonly found in bone mills facilitates the retention of bone particles, which can hamper the effectiveness of the cleaning process, furthering the possibility of contamination during subsequent use of the bone mill.

In addition to reduced availability and the inconveniences and costs associate with sterilizing requirements, existing bone mills are typically powered devices that require an external means for driving the mill, such as a pressurized air source or an electrical motor. Such powered devices often operate at high RPMs, which generate significant amounts of heat that can compromise or otherwise destroy the healing properties of a tissue sample. Additionally, existing mills may only have the capability to produce a single size of crushed bone particles. As such, a surgical suite needs to have multiple devices to provide crushed bone at different sizes, which greatly increases the cost of having bone-milling capabilities. Otherwise, a surgeon is disadvantageously forced to use crushed bone having a size either too large or too small for a particular surgical procedure, resulting in potential difficulties and reduced efficacy.

In view of the above limitations, it is therefore desirable to have an inexpensive tissue processing device that can either be disposed after each use easily sterilized, can create processed tissue specimens having a desired range of sizes, and can also be manually operated with ease.

SUMMARY OF THE INVENTION

The present invention advantageously provides an inexpensive tissue processing device that can either be disposed after each use easily sterilized, can create processed tissue specimens having a desired range of sizes, and can also be manually operated with ease. In particular, a tissue processing device is provided that includes a housing defining a first passage through at least a portion thereof, the first passage defining a longitudinal axis; a first processing member rotatably coupled to the housing and extending across at least a portion of the first passage; and a second processing member rotatably coupled to the housing and extending across at least a portion of the first passage, the second processing member being substantially parallel to the first processing member, the second member being offset from the first processing member in a first direction substantially parallel to the longitudinal axis and in a second direction substantially transverse to the longitudinal axis. The device may include a manual actuation element coupled to at least one of the first and second processing members such that rotation of the actuation element causes rotation of the first and second processing member and/or a gear removably engageable between the manual actuation element and the at least one of the first and second processing members to provide a preselected mechanical advantage between the manual actuation element and the at least one of the first and second processing members. The first processing member may rotate in a direction opposite to a direction of rotation of the second processing member in use. The device may include a first gear coaxial with the first processing member; and a second gear coaxial with the second processing member, with the first gear engaging the second gear. The first gear and second gear may have different sizes compared to one another. The device may also include a receptacle releasably engageable with the housing adjacent the first passage, where the receptacle defines a cavity for receiving processed tissue from the first passage, with the receptacle including a divider that segments a portion of the cavity. The device may include a second passage intersecting the first passage at a location between the first processing member and the receptacle. The first processing member may define a substantially smooth helical groove extending along a length thereof and/or a helical segment having a plurality of teeth extending along the length thereof. The second processing member may define a substantially smooth helical groove extending along a length thereof, where the helical groove of the second processing member has a pitch opposite to a pitch of the helical groove of the first processing member, and the second processing member may define a helical segment having a plurality of teeth extending along the length thereof. The housing of the device may define a base and an upper portion angled with respect to the base.

A bone mill is provided, including a body defining a first portion and a second portion angled with respect to the first portion, the body defining a substantially linear passage extending through at least a part of the first and second portions; first and second milling members extending across a portion of the passage; a knob rotatably attached to the first portion of the body and coupled to at least one of the first and second milling members; a cover positionable on the first portion of the body, the cover extending into at least a portion of the passage; and a receptacle removably positionable within the second portion of the body to receive milled bone from the passage. The first and second milling members may each define a substantially smooth helical groove extending along a length thereof, and the receptacle may define a cavity and a divider that segments a portion of the cavity. The bone mill may include a gear component removably engageable between the knob and at least one of the first and second milling members and/or a plurality of interchangeable gear components, each of the plurality of interchangeable gear components providing a predetermined turning ratio between the knob and the first and second milling members.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
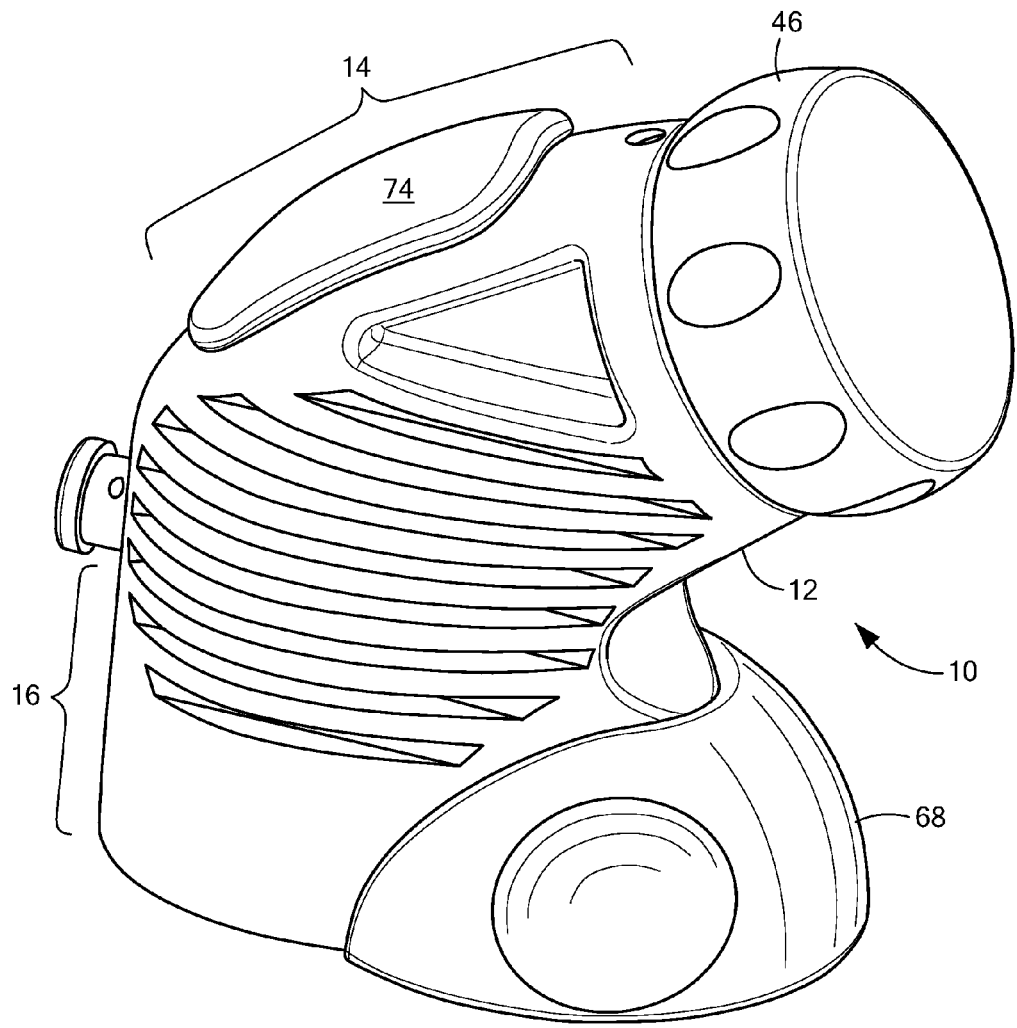
FIG. 1 is a perspective view of an embodiment of a tissue processing device constructed in accordance with the principles of the present invention.
Figure 2:
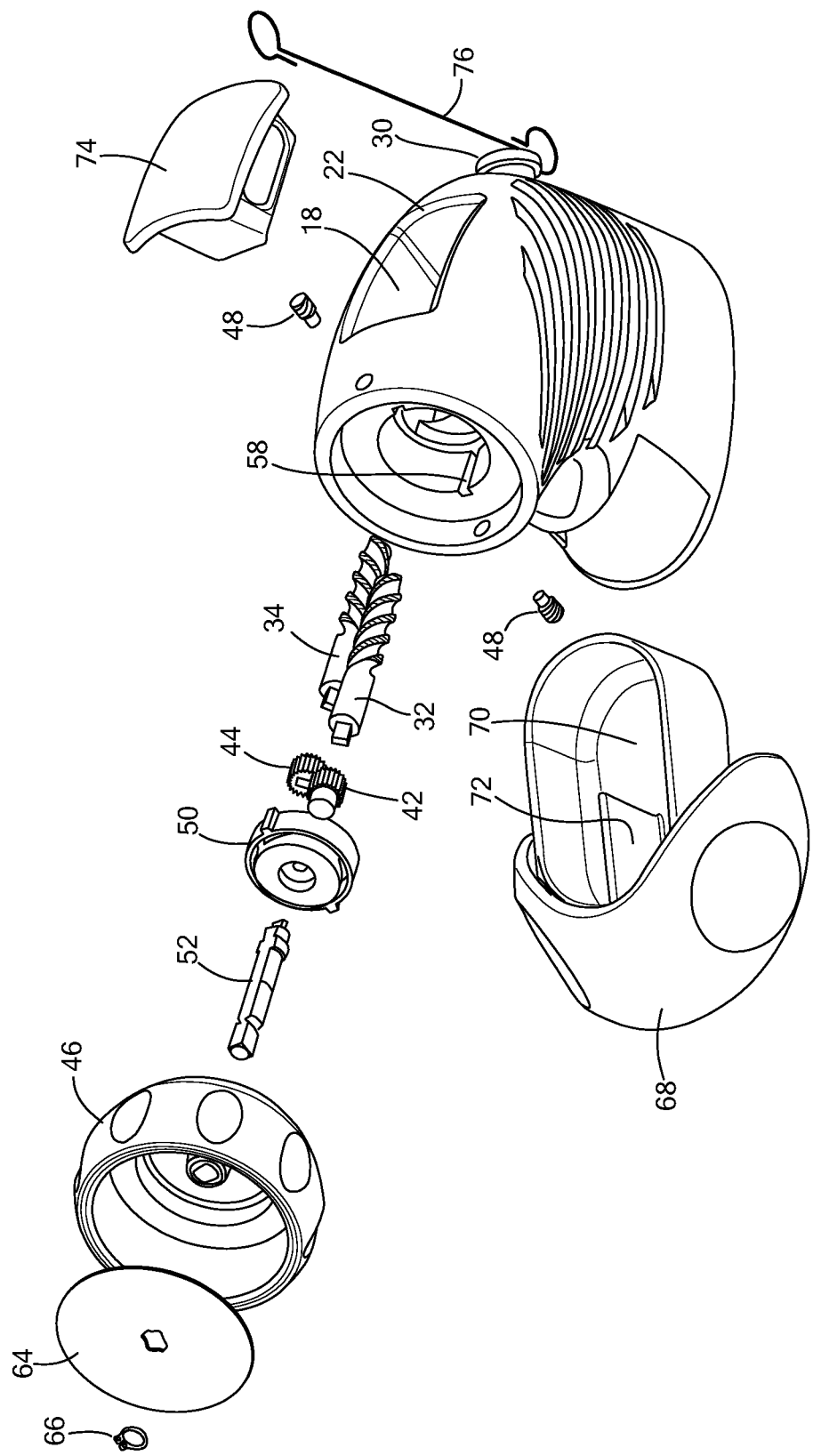
FIG. 2 is an exploded assembly view of the tissue processing device of FIG. 1.
Figure 3:
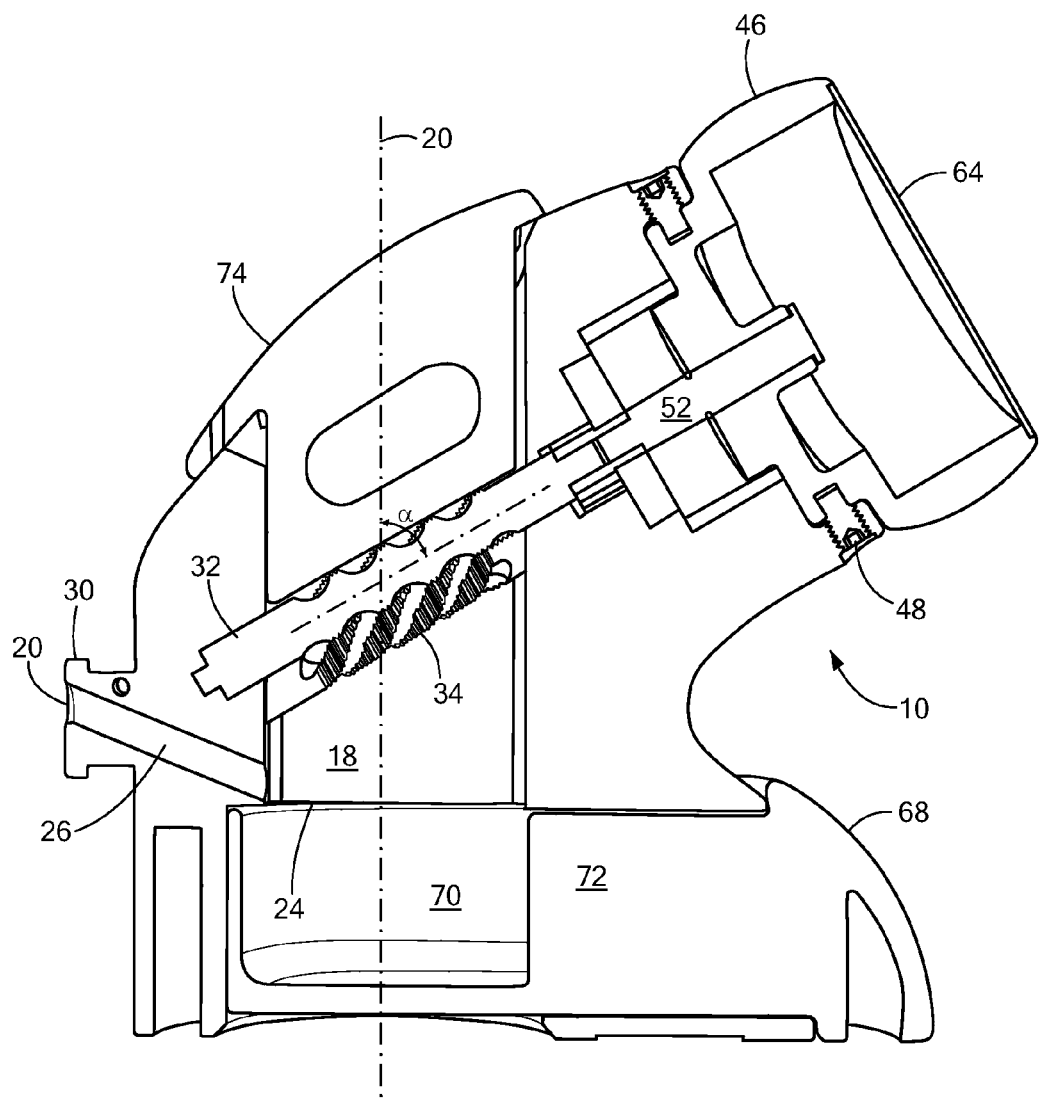
FIG. 3 is a cross-sectional view of the tissue processing device of FIG. 1.

The present invention advantageously provides an inexpensive tissue processing device, such as a bone mill, that can either be disposed after each use easily sterilized, can create processed tissue specimens having a desired range of sizes, and can also be manually operated with ease. Referring now to the drawing figures in which like reference designations refer to like elements, an embodiment of a tissue processing device constructed in accordance with principles of the present invention is shown in FIGS. 1-3 and generally designated as "10." Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

The tissue processing device 10 may generally include a device body or housing 12. The housing 12 may generally define a first, upper portion 14 and a second, base portion 16. The first portion 14 may include one or more controls or actuation features for operating the device 10, as described in more detail below, while the second portion 16 provides a stable base or platform to allow the device 10 to be free-standing on a table top. In addition, the first portion 14 may extend from or otherwise protrude from the second portion of the housing 12 at an angle. The angled orientation provides an overall ergonomic shape such that the device 10 is easily grasped in one hand while allowing operation or actuation of the device 10 with the other hand in a secure and comfortable manner.

Referring now to FIGS. 2-3, the body or housing 12 may define a first passage 18 for the receipt, processing, and dispersal of a tissue specimen or sample. The first passage 18 may be substantially linear along a height of the device 10 body or housing 12 and define a longitudinal axis 20. The first passage 18 may generally extend through at least a segment of the first and second portions of the housing 12, beginning at a first opening 22 on a segment of the upper, first portion 14 of the housing 12, and leading to a second opening 24 in the second, base portion 16 of the housing 12.

The housing 12 may further include a second passage 26 allowing the introduction of one or more biological, pharmaceutical, or other healing, growth-promoting agents into tissue processed by the device 10. The second passage 26 may have an opening 28 on an exterior surface of the housing 12 and further extend into or otherwise intersect the first passage 18 in the second, base portion of the housing 12. The second passage 26 may include a flange 30 that facilitates the engagement to or insertion of a syringe or other agent-delivery apparatus with the second passage 26.

The tissue processing device 10 further includes first and second tissue processing or milling members 32, 34 at least partially disposed in the first passage 18 to mill, cut, or otherwise process a tissue specimen inserted into the first passage 18. The first and second tissue processing members 32, 34 may be rotatably coupled to the housing 12 and extend across the first passage 18 in an angled orientation. In addition, the first tissue processing member 32 may be offset from the second tissue processing member 34 in at least two directions. For example, the second tissue processing member 34 may be offset from the first member 32 along the longitudinal axis 20, e.g., lower than the first tissue processing member 32 for example. The second tissue processing member 34 may also be offset from the first tissue processing member 32 in a direction transverse to the longitudinal axis 20 (e.g., to the left or right, for example). The first and second tissue processing members 32, 34 may also be angularly positioned within the first passage. For example, the first and second processing members may define an angle α with the longitudinal axis 20 between approximately 45° and 70°. The angled orientation of the tissue processing members increase the shearing effect the members 32, 34 exert on a tissue specimen, which reduces the effort needed to process a particular sample, as described in more detail below.

Figure 4:
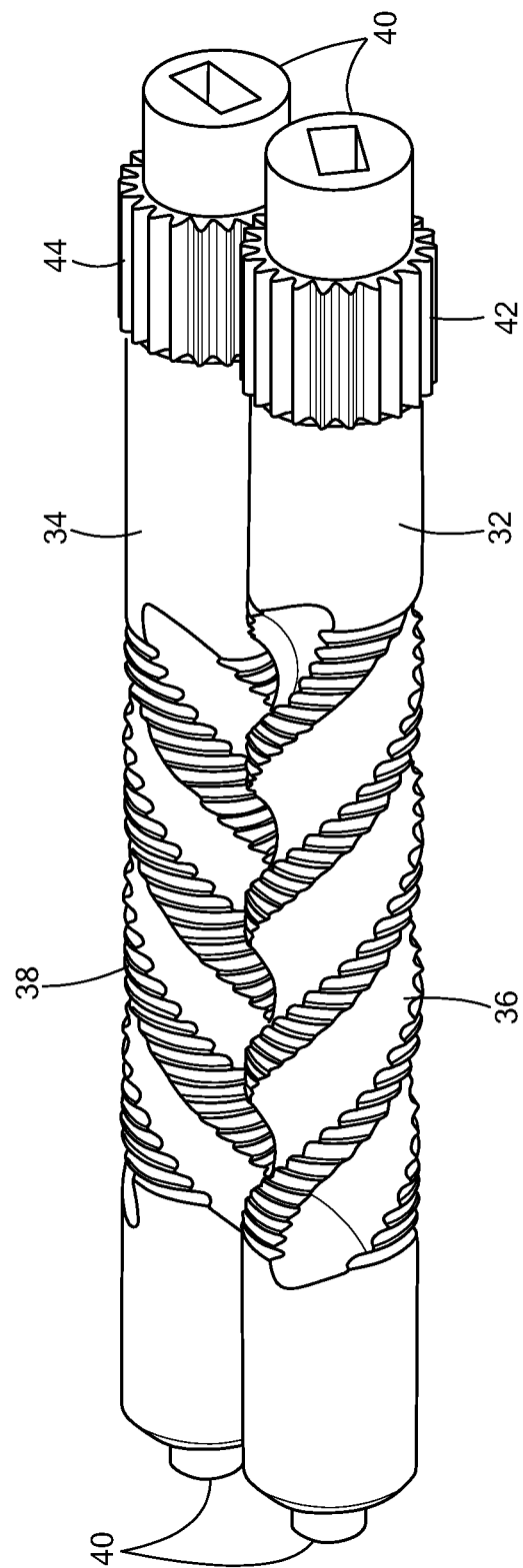
FIG. 4 is an illustration of processing members for a tissue processing device constructed in accordance with the principles of the present invention.

As shown in FIG. 4, each tissue processing member may define an elongate body having a generally cylindrical shape. The first and second tissue processing members may each define a substantially smooth, helical groove 36 extending along its length, as well as a helical segment or winding 38 having raised ridges or teeth. The tissue processing members 32, 34 may also include one or more protrusions or engagement features 40 facilitating placement and coupling to the other portions of the device 10.

The first and second processing members 32, 34 may be coupled to one another so that rotation of one of the members causes rotation of the other in an opposite direction. For example, a first gear 42 may be mounted on or otherwise extend from the first tissue processing member 32. A second gear 44 may be mounted on or otherwise coupled to the second tissue processing member 34, and may be further engaged to the first gear 42 either directly or indirectly through one or more intermediary gears or force transmission mechanisms (not shown). In the direct engagement between the first and second gears shown in FIG. 4, rotation of the first tissue processing member 32 in a first direction (e.g., clockwise for example) will result in the rotation of the second member 34 in a second direction opposite from the first direction (e.g., counter-clockwise, for example). The sizes of the first and second gears may be varied either uniformly or relative to each other to provide a desired positional offset between the tissue processing members and/or to provide varying turning ratios between the first and second tissue processing members, respectively.

Referring again to FIGS. 1-3, the tissue processing device 10 may include an actuation element 46 or component attached to the housing 12 and at least one of the first and second tissue processing members 32, 34 for the operation thereof. For example, the actuation element 46 may include a knob rotatably coupled to the first portion 14 of the housing 12. The actuation element 46 may be releasably secured to the housing 12 by one or more anchors or set screws 48 that prevent the actuation element 46 from disengaging the housing 12 during use, but still allowing the desired rotational operation. The actuation element 46 may have a generally circular or cylindrical shape, and may further have an outer diameter significantly larger than either of the first and second tissue processing members to impart a mechanical advantage easing use of the device 10 when strong, dense materials or specimens are being processed or milled with the device 10.

Figure 5:
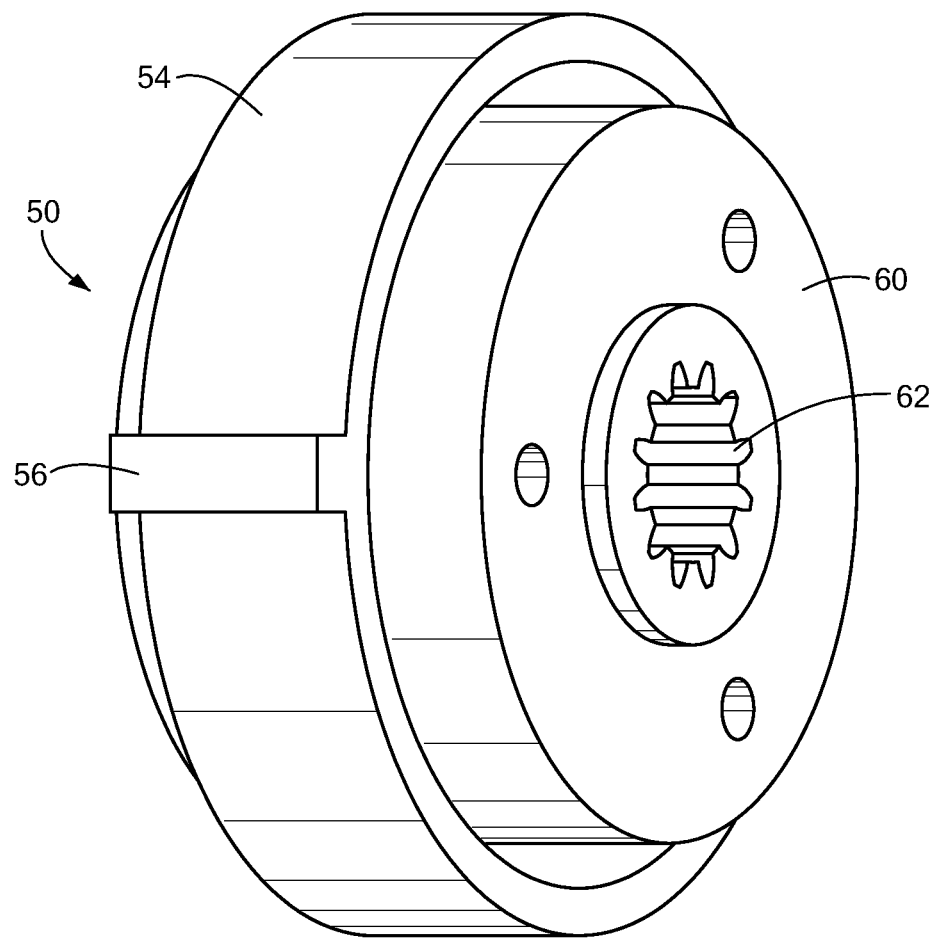
FIG. 5 is an illustration of a gear component for a tissue processing device constructed in accordance with the principles of the present invention.

The actuation element 46 may be coupled to at least one of the first and second tissue processing members 32, 34 either directly or through one or more intermediary transmission or gearing components providing varying ranges of mechanical advantage and/or turning rations between the actuation element 46 and the processing members. For example, as shown in FIGS. 2 and 5, the tissue processing device 10 may include a gear component 50 coupled to the actuation element 46 by a shaft 52 such that rotation of the actuation element 46 results in the rotation of at least a portion of the gear component 50. The gear component 50 may include an outer frame 54 that is securely engageable or positionable within the first portion 14 of the housing 12. The outer frame 54 may include one or more protrusions or anchors 56 that couple to complementary slots 58 defined in the housing 12, which prevents the rotation of the outer frame 54 with respect to the housing 12. The gear component 50 may further include an inner frame or segment 60 that is rotatable within the outer frame 54. A first side of the inner frame or segment 54 may be engageable to the shaft 52, while an opposite side of the inner segment 60 may be engageable with either of the first and second tissue processing members 32, 34. For example, the opposite side may define a ridged gear interface 62 that engages a portion of the first gear 42, e.g., such as that in a planetary gear coupling for example. The relative size of the gear interface 62 to the first gear 42 dictates the turning ratio (i.e., the number of turns the first gear experiences for every turn of the gear component) between the gear component 50 and the first gear 42. The diameter of the gear interface 62 thus affects the turning ratio between the actuation element 46 and the first and second tissue processing elements 32, 34. Accordingly, the device 10 may include a plurality of interchangeable gear components having varying diameters to impart a selected turning ratio and/or mechanical advantage for a specified use or tissue specimen.

Where a simple 1:1 turning ratio is desired, the gear component 50 may be removed, and the actuation element 46 may be directly coupled to the first and/or second tissue processing members by the shaft 52, as shown in FIG. 3. The actuation element 46 may be slidably engaged to the shaft and secured in place by a cap 64 and/or securing ring 66, as shown in FIG. 2.

Alternatively, the actuation element 46 may be removed from the housing 12, and a powered drive element (such as a pneumatic coupling, electrical rotary tool, or the like) can be directly coupled to the shaft and/or gear component to allow the tissue processing device 10 to be power operated with caution that the RPMs do not result in excessive, damaging heat generation to the tissue specimen being processed.

Now referring to FIGS. 1-3, the tissue processing device 10 may include a receptacle 68 removably positionable within or about the second portion of the housing 12 to receive processed material or contents from the first passage 18. The receptacle 68 may define a cavity or chamber 70 positioned adjacent an outlet or opening of the first passage 18 to contain the received milled or processed material. The receptacle 68 may further include a divider or wall 72 that segments one portion of the cavity 70 from another. The divider 72 may extend along all or a part of a length of the cavity 70, and allows a user or physician to divide the milled, processed contents from the device 10 into substantially equally amounts for procedures involving the application of processed material to more than one site.

A cover 74 may be include with the tissue processing device 10 to both aid in directing a tissue specimen towards the tissue processing members as well as preventing any unwanted materials or items from entering the first passage 18 when the device 10 is not in use. For example, the cover 74 may be positionable across the first portion 14 of the housing 12 to completely cover or obstruct access to the first passage 18 when the cover is in place. A portion of the cover 74 may also extend into the first passage 18 towards the first and second tissue processing members to push unmilled specimens towards the processing members without the cover 74 itself contacting the tissue processing members 32, 34. The cover 74 may also be tethered to the housing 12 by a cord or cable 76, which may couple to the housing 12 at or near the flange 30, for example.

In an exemplary use of the tissue processing device 10, a tissue specimen, such as a harvested bone sample, may be milled or processed for subsequent use in a surgical procedure. Depending on the particular specimen characteristics, a suitable gear component 50 may be inserted into the housing 12 between the actuation element 46 and the tissue processing members 32, 34 to achieve a desired mechanical advantage and/or turning ratio. The specimen may then be directed into the first passage 18, with the cover 74 then placed over the first passage 18 to direct the specimen towards the tissue processing members 32, 34. The actuation element 46 may then be rotated, resulting in the rotation of the first and second tissue processing members to process or mill the specimen.

Of note, the features and orientation of the tissue processing members 32, 34 facilitate both ease of use of the device 10 as well as providing a consistent, desired processed result. In particular, the first and second tissue processing members may be angled with respect to the longitudinal axis 20 (and a transverse axis). This angled orientation results in an increase in the shearing force exerted on the specimen directed into the device 10, which reduces the effort needed to process a particular tissue specimen. The bi-directional offset between the first and second tissue processing members further increases the shearing action of the device 10, while the counter rotational movement between the first and second tissue processing members results in the first tissue processing member 32 pulling or directing a tissue specimen into the region between the two processing members, reducing the force needed on the cover 74 to push a specimen through the first passage 18. In addition, the combination of the smooth helical grooves 36 and ridged helical segments 38 on the first and second tissue processing members results in repeatably-obtainable, predictable variations in particle size for the milled material exiting the device 10. In particular, the space created between the respective smooth helical segments 36 of the tissue processing members results in particles of a first size passing through, for example, 5 mm. The space between the respective helical teeth segments 38 of the tissue processing members has a reduced clearance or is otherwise smaller than the clearance between the smooth helical segments 36, which results in particles or milled material having smaller sizes, such as 2 mm for example. The 2 mm-5 mm size range of milled particles has been indicated as providing a desirable consistency and applicability in bone grafts for varying orthopedic procedures compared to other sizes, which may result in either the milled material being too fine to manipulate into a surgical site, or too large, which may result in similar difficulties in applying and/or conforming a milled material to a designated surgical site.

Once the tissue specimen had been processed or milled by the first and second tissue processing elements, it may descend downward through the first passage 18 and into the receptacle 68. One or more biological and/or pharmaceutical agents may also be introduced into the milled material and/or receptacle 68 through the second passage 26, which disperses into the first passage 18 between the processing members and the receptacle 68. Once a suitable amount of material or tissue has been milled or otherwise processed by the device 10, the receptacle 68 may be removed, the contents of the receptacle 68 may be mixed with the introduced agent, and/or the milled material may be divided within the receptacle 68 by the divider 72. The user may then proceed to apply the milled material in accordance with particular procedure undertaken.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A tissue processing device, comprising:
    a housing defining a first passage and a second passage, each of the first and second passages extending through at least a portion of the housing, the first passage defining a longitudinal axis;
    a receptacle releasably engageable with the housing adjacent the first passage;
    a first processing member rotatably coupled to the housing and extending across at least a portion of the first passage, the second passage intersecting the first passage at a location between the first processing member and the receptacle; and
    a second processing member rotatably coupled to the housing and extending across at least a portion of the first passage, the second processing member being substantially parallel to the first processing member, the second processing member being offset from the first processing member in a first direction substantially parallel to the longitudinal axis and in a second direction substantially transverse to the longitudinal axis.

2. The tissue processing device of claim 1, further comprising a manual actuation element coupled to at least one of the first and second processing members such that rotation of the actuation element causes rotation of the first and second processing members.

3. The tissue processing device of claim 2, further comprising a gear removably engageable between the manual actuation element and the at least one of the first and second processing members to provide a preselected mechanical advantage between the manual actuation element and the at least one of the first and second processing members.

4. The tissue processing device of claim 2, wherein the first processing member rotates in a direction opposite to a direction of rotation of the second processing member.

5. The tissue processing device of claim 1, further comprising:
    a first gear coaxial with the first processing member; and
    a second gear coaxial with the second processing member, the first gear engaging the second gear.

6. The tissue processing device of claim 5, wherein the first gear and second gear have different sizes.

7. The tissue processing device of claim 1, wherein the receptacle defines a cavity for receiving processed tissue from the first passage, the receptacle including a divider that segments a portion of the cavity.

8. The tissue processing device of claim 1, wherein the first processing member defines a substantially smooth helical groove extending along a length thereof.

9. The tissue processing device of claim 8, wherein the first processing member defines a helical segment having a plurality of teeth extending along the length thereof.

10. The tissue processing device of claim 8, wherein the second processing member defines a substantially smooth helical groove extending along a length thereof.

11. The tissue processing device of claim 10, wherein the helical groove of the second processing member has a pitch opposite to a pitch of the helical groove of the first processing member.

12. The tissue processing device of claim 10, wherein the second processing member defines a helical segment having a plurality of teeth extending along the length thereof.

13. The tissue processing device of claim 1, wherein the housing defines a base and an upper portion angled with respect to the base.

* * * * *